United States Patent
Batchelor et al.

(10) Patent No.: US 6,827,725 B2
(45) Date of Patent: Dec. 7, 2004

(54) SURGICAL INSTRUMENT

(75) Inventors: Kester J. Batchelor, Newport (GB); Julian M. Ebbutt, Cardiff (GB)

(73) Assignee: Gyrus Medical Limited, Cardiff (GB)

(*) Notice: Subject to any disclaimer, the term of this patent is extended or adjusted under 35 U.S.C. 154(b) by 225 days.

(21) Appl. No.: 10/139,638

(22) Filed: May 7, 2002

(65) Prior Publication Data

US 2002/0173776 A1 Nov. 21, 2002

Related U.S. Application Data

(60) Provisional application No. 60/305,097, filed on Jul. 16, 2001.

(30) Foreign Application Priority Data

May 10, 2001 (GB) .............................................. 0111463

(51) Int. Cl.[7] .............................................. A61B 17/32
(52) U.S. Cl. ....................................................... 606/170
(58) Field of Search ................................ 606/170, 179, 606/180, 159, 41, 46, 48, 50; 604/22

(56) References Cited

U.S. PATENT DOCUMENTS

| | | | | |
|---|---|---|---|---|
| 3,828,780 A | * | 8/1974 | Morrison, Jr. ............... 604/20 |
| 4,850,354 A | * | 7/1989 | McGurk-Burleson et al. ............. 606/170 |
| 5,027,792 A | * | 7/1991 | Meyer ......................... 600/104 |
| 5,085,658 A | * | 2/1992 | Meyer .......................... 606/46 |
| 5,364,395 A | * | 11/1994 | West, Jr. ....................... 606/46 |
| 5,527,331 A | * | 6/1996 | Kresch et al. ............... 606/170 |
| 5,904,681 A | * | 5/1999 | West, Jr. ....................... 606/41 |
| 6,193,715 B1 | * | 2/2001 | Wrublewski et al. .......... 606/45 |
| 6,482,202 B1 | * | 11/2002 | Goble et al. ................... 606/41 |

* cited by examiner

*Primary Examiner*—Michael J. Milano
*Assistant Examiner*—Victor Nguyen
(74) *Attorney, Agent, or Firm*—Nixon & Vanderhye P.C.

(57) ABSTRACT

A surgical instrument includes an elongate hollow probe having first and second apertures (4 and 5) at its distal end portion. An elongate drive shaft disposed within the probe (1) and mounted for rotation about its longitudinal axis within the probe. A cutting tool (2, 34) is located at the distal end of the drive shaft, and is positioned adjacent to the first aperture (4). A bipolar electrosurgical device (3) is located at the distal end of the probe (1) in the region of the second aperture (5). The electrosurgical device includes an active electrode (13) and a return electrode (11) separate and insulated therefrom. A motor (6) is provided for rotating the drive shaft; and suction means is provided for selectively providing a source of suction at either the first apertures (4) or the second aperture (5).

19 Claims, 3 Drawing Sheets

SURGICAL INSTRUMENT

This application claims the benefit of Provisional Application No. 60/305,097 filed Jul. 16, 2001, the entire content of which is hereby incorporated by reference in this application.

This invention relates to a surgical instrument, and in particular to a surgical instrument that can use mechanical energy and/or electrical energy to treat tissue.

Known mechanical surgical instruments include simple scalpels which are used for cutting soft tissue, rotatable shavers which are also used for removing soft tissue, and rotatable burrs which are used for cutting harder tissue such as bone.

Known electrosurgical instruments include monopolar and bipolar devices, both of which are used primarily for treating or cauterising soft tissue. A monopolar electrosurgical device includes a single active electrode and a return electrode, the return electrode being positioned, in use, remotely from the active electrode, usually on the patient's skin. A bipolar electrosurgical instrument has both active and return electrodes located in close proximity, usually within the one device. Electrical energy passes from the active electrode to the return electrode via tissue being treated, and possibly via an electroconductive fluid surrounding the tip of the instrument. Both monopolar and bipolar electrosurgical instruments are limited by their inability to remove hard tissue such as bone, as they are less efficient and relatively slow in removing such hard tissue.

Typically, therefore, if a surgeon needs to remove hard and soft tissues from the same surgical site, and/or to cauterise and/or to ablate tissue, different surgical instruments would need to be used. For example, an electrosurgical instrument could be used to cut soft tissue, in which case a mechanical instrument (such as a burr) would be needed to cut hard tissue such as bone. The insertion and removal of different surgical instruments through an incision to a surgical site does, however, complicate and lengthen a surgical operation as compared with using a single surgical instrument, as well as adding to the overall costs of instruments needed.

To overcome this disadvantage, it is known to use a surgical instrument which includes a mechanical element, such as a rotary shaver or burr, and an electrosurgical instrument such as a monopolar or bipolar device. A known instrument of this type is described in U.S. Pat. No. 5,904,681, which describes an instrument having a shaver or burr rotatably mounted within an outer sleeve, and a bipolar electrosurgical device mounted at the end of the outer sleeve and adjacent to an apertured end portion thereof through which the rotary shaver or burr acts on hard tissue such as bone. The interior of the sleeve is connected to a source of suction, so that tissue particles removed by the shaver or burr can be removed from the vicinity of the surgical site. The disadvantage of this type of instrument is that tissue debris removed by the electrosurgical device cannot be removed from the vicinity of the surgical site via the sleeve interior by the source of suction provided for removing tissue particles cut by the rotary shaver or burr.

The aim of the invention is to provide a surgical instrument that can cut through both soft and hard tissues using mechanical and electrosurgical devices, and reliably remove tissue particles and debris produced by both the mechanical and electrosurgical means.

The present invention provides a surgical instrument comprising an elongate hollow probe having an apertured region at its distal end portion, an elongate drive shaft disposed within the probe and mounted for rotation about its longitudinal axis within the probe, a cutting tool located at the distal end of the drive shaft and positioned adjacent to the apertured region, an electrosurgical device located at the distal end of the probe adjacent to the apertured region, a motor for rotating the drive shaft, and suction means for providing a source of suction at the apertured region for evacuating tissue debris removed by either the cutting tool or the electrosurgical device Advantageously, the electrosurgical device is a bipolar electrosurgical device including at least one active electrode, at least one return electrode and an insulator for spacing and insulating the or each return electrode with respect to the or each active electrode.

In a preferred embodiment, the apertured region is constituted by first and second apertures, the cutting tool being positioned to enable tissue to be cut by cutting means provided on the cutting tool, the cutting means being engageable with tissue through the first aperture, and the second aperture being positioned in the region of the electrosurgical device, preferably adjacent thereto.

In a preferred embodiment, the instrument further comprises means for selectively blocking communication between the first aperture and the suction means to allow the suction means to operate principally through the second aperture. In one embodiment, the drive shaft is hollow, the cutting tool is hollow and contiguous therewith, and the distal end portion of the cutting tool is formed with a cut-out through which tissue debris can be evacuated when the cut-out is in alignment with the first aperture. Alternatively, the drive shaft is solid and of a diameter less than that of the hollow probe so as to define a channel between the drive shaft and the hollow probe, tissue debris being removable via the channel.

Advantageously, the blocking means is provided by the cutting tool being configured in such a manner that a portion thereof effectively blocks the first aperture when the cutting tool is in a predetermined rotational position. Preferably, an outer surface of the hollow cutting tool constitutes the means for effectively blocking the first aperture when the cutting tool is in said predetermined position. In one preferred arrangement, the instrument further comprises means for selectively positioning the cutting tool automatically in said predetermined position.

Alternatively, the blocking means comprises a baffle operable to block effectively the first aperture. The baffle may be located on the interior or the exterior of the probe, and is preferably movable between a first position, in which it effectively blocks the first aperture, and a second position in which it is clear of the first aperture. In one arrangement, the baffle is rotatable about the longitudinal axis of the probe between the first and second positions. The baffle may be manually movable between its first and second positions, or alternatively a motor is provided to move the baffle between its first and second positions.

Alternatively, the cutting tool is provided with an abrasive outer surface, the distal end portion of the probe being spaced from the abrasive outer surface to define an inlet through which tissue debris can pass.

Conveniently, there is a single active electrode, and a single return electrode, and the active electrode, the insulator and the return electrode are formed with contiguous apertures in alignment with the second aperture.

The invention will now be described in greater detail, by way of example, with reference to the drawings, in which FIG. 1 is a schematic diagram of a surgical system incorporating a surgical instrument constructed in accordance with the invention;

Figure 1:
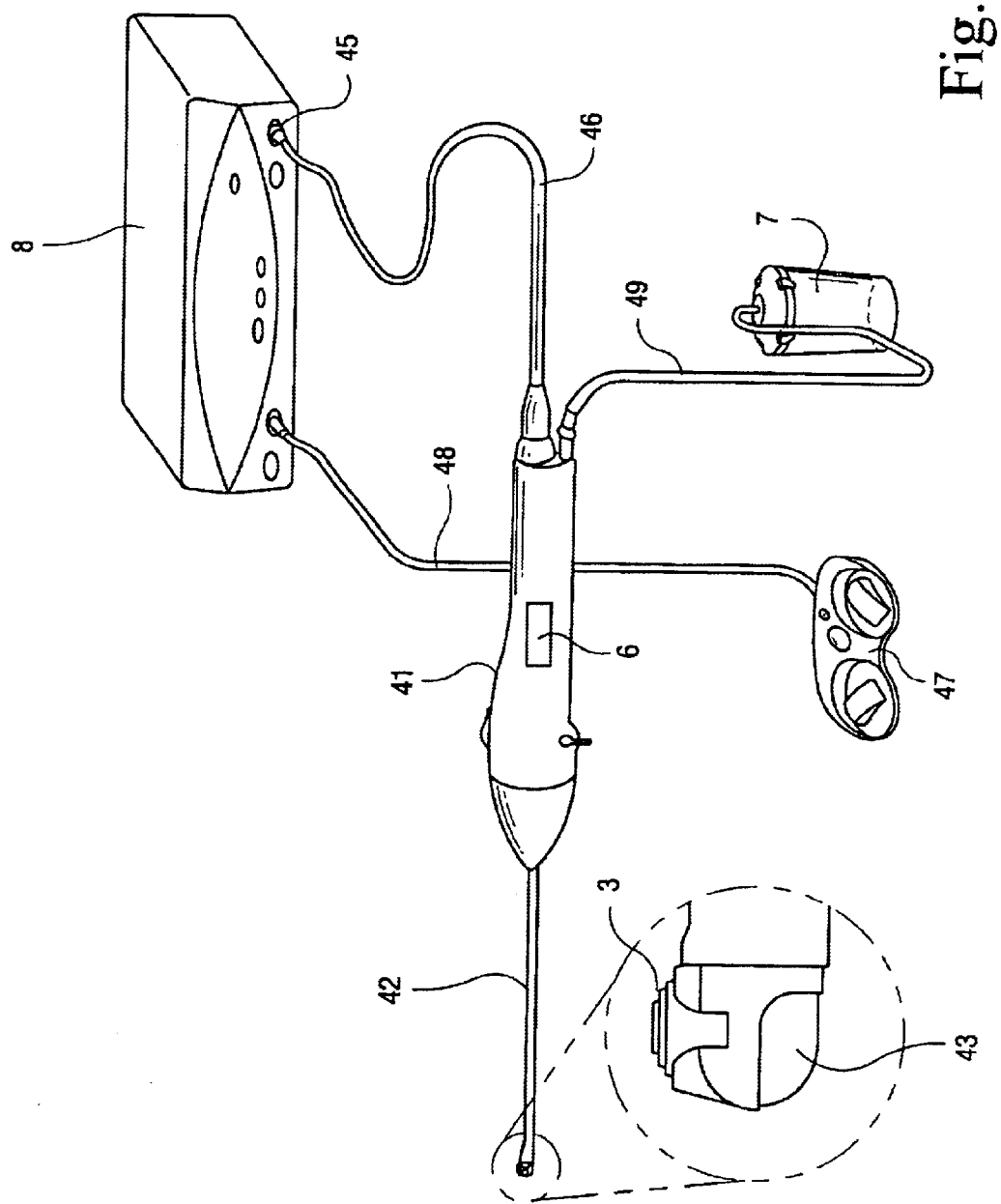

Referring to the drawings, FIG. 1 shows an electrosurgical system which includes a controller/generator 8 and a handpiece 41 having a detachable surgical probe shown generally at 42. The probe 42 includes both a rotatable cutting element 43, driven by a motor, shown schematically at 6, within the handpiece 41, and a bipolar electrosurgical device shown generally at 3. Power signals for both the motor 6 and the electrosurgical device 3 are supplied to the handpiece 41 from an output socket 45 on the controller/generator 8, via a connector cord 46. Activation of the controller/generator 8 may be performed by means of a footswitch 47, coupled to the controller/generator by means of a connector cord 48. A source of suction 7 is also provided, coupled to the handpiece by a cord 49.

Figure 2:
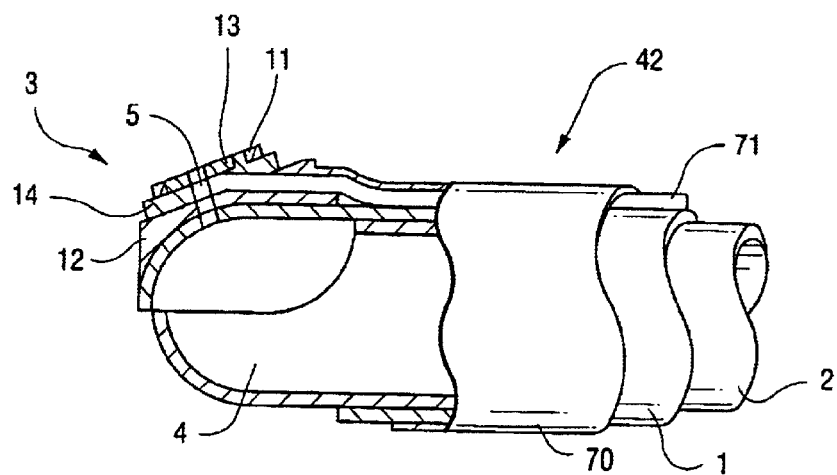
FIG. 2 is a side view. partly in section, of the distal end of a surgical instrument constructed in accordance with the invention.

FIG. 2 shows the distal end of the surgical probe 42 which has a generally cylindrical outer tube 1, a mechanical shaver 2 rotatably mounted within the outer tube, and the bipolar electrosurgical device 3 fixed to an external surface of the tube. The tube 1 is made of a conductive metal such as stainless steel, and its external surface is substantially coated with an insulating material such as an insulating polymer sheath. The extreme distal end portion of the tube 1 is formed with a cut-out 4 through which the distal end portion of the shaver 2 protrudes. The shaver 2 is rotatable, relative to the tube 1, by the motor 6 which is a brushless dc motor. The shaver 2 is generally hollow, and the suction pump 7 applies suction to the interior of the shaver, and hence to the region surrounding the cut-out 4.

The bipolar electrosurgical device 3 comprises a return electrode 11 which is secured to the outer tube 1 and mounted on a spacing element 12, and an active (tissue treatment) electrode 13 spaced from the return electrode by a ceramic insulator 14. Contiguous apertures 5 in the tube 1, the return electrode 11, the insulator 14 and the tissue treatment electrode 13 constitute a passage leading from the interior of the tube 1 to the region adjacent to the tissue treatment electrode. Through the apertures 5, suction can be applied to the region surrounding the tissue treatment electrode 13. The electrosurgical controller/generator 8 supplies radio frequency (RF) power to the bipolar electrosurgical device, electrical current passing to the tissue treatment electrode 13 via a lead 71.

The surgical instrument described above is intended for arthroscopic use, that is to say for operations on joints such as shoulders or knees. It will be appreciated, however, that the surgical instrument could be used at any surgical site located within the body of a patient where surgery is to be performed. Moreover, the surgical instrument is primarily intended for use with an endoscope which allows a surgeon to view a surgical site. In such a case, the surgical instrument is inserted through a first incision, and the endoscope is inserted through a second incision. The distal ends of both the endoscope and the surgical instrument are positioned adjacent to the surgical site, and the surgeon can view the surgical site on a monitor attached to the endoscope.

In use, once the endoscope and surgical instrument have been positioned adjacent to the surgical site, the dc motor 6 is turned on to power the rotatable shaver 2, which can then be used to remove tissue from the surgical site. Any tissue or debris removed in this mechanical surgical procedure is extracted from the region of the surgical site via the cut-out 4 in the tube 1, and the interior of the shaver by the suction pump 7.

When the surgeon has finished using the shaver 2, he can use the electrosurgical device 3 to ablate or desiccate soft tissue at the site, or to cauterise adjacent blood vessels. In order to do this, the controller/generator 8 switches off the dc motor 6, and electrosurgical power is provided to the electrosurgical device 3. The electrosurgical device 3 can ablate, desiccate or cauterise at the surgical site. Any tissue removed during such an operation, can be removed by the suction pump 7 via the apertures 5 and the interior of the shaver 2.

The surgical instrument described above can, therefore, be used for both mechanical and electrosurgical operation, so a single instrument can be used for both types of surgery, thereby avoiding the need to use two different instruments for surgery involving treatment of both hard and soft tissue. Moreover, the provision of the apertures 4 and 5 in the distal end of the tube 1 and the tissue treatment electrode 13 respectively ensures that suction can be applied to the regions of mechanical and electrosurgical tissue treatment to facilitate the removal of surgically-removed tissue debris.

As the cut-out 4 is considerably larger in area than the apertures 5, suction power in the region of the tissue treatment electrode 13 will be substantially reduced during electrosurgery unless the cut-out 4 is blocked off. It is important, therefore, when the dc motor 6 is turned off and the electrosurgical power is supplied to the device 3, that the shaver 2 is positioned within the tube 1 so as to completely block the cut-out 4. This can be accomplished by shaping the distal end portion of the shaver 2 so as to block the cut-out 4 when the shaver is in the "RF mode" position shown in FIG. 2, and by controlling the motor 6 to bring the shaver to the RF mode position when an appropriate signal is provided by the controller/generator 8.

Figure 3:
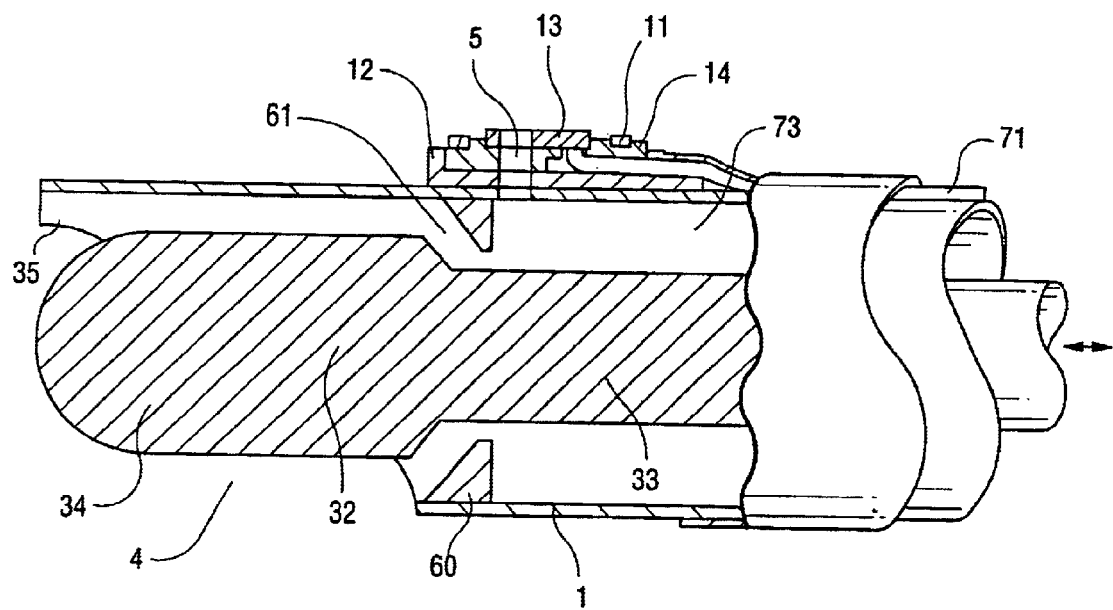
FIG. 3 is a side view, partly in section, of an alternative embodiment of a surgical instrument constructed in accordance with the invention.

FIG. 3 shows the distal end of a modified form of the surgical instrument of FIG. 2. This surgical instrument is similar to that of FIG. 2, and so like reference numerals will be used for like parts, and only the modifications will be described in detail. The basic difference between the surgical instrument of FIG. 3 and that of FIG. 2 is that this surgical device includes a mechanical burr 32 in place of the mechanical shaver 2. The burr 32 has a hollow central stem 33 which is rotatably mounted within the outer tube 1, and a solid cutting head 34 having an abrasive outer surface. The cutting head 34 extends through the cut-out 4 in a distal end portion of the tube 1 so that, in use, the abrasive outer surface can contact hard tissue or bone for mechanical removal thereof. The distal end of the tube 1 protrudes from the distal end of the cutting head 34 to define therewith an inlet 35 through which tissue debris can pass. The inlet 35 communicates with a passageway 73 between the stem 33 and the outer tube 1, so that the suction pump 7 can provide suction to the inlet 35.

An annular valve seat 60 is located on the inner surface of the outer tube 1, at a position corresponding with the transition from the stem 33 to the cutting head 34, and just distal of the apertures 5. In its rotating position (shown in FIG. 3), the burr 32 is spaced longitudinally from the valve seat 60 such that there is an annular aperture 61 between the stem 33 and the outer tube 1 allowing communication between the inlet 35 and the passageway 73. In this way, suction is delivered to the inlet 35. However, when it is desired to use the electrosurgical device 3, the burr 32 is moved longitudinally in the outer tube 1 so that the cutting head 34 contacts the valve seat 60, closing the annular aperture 61. Now there is no communication between the inlet 35 and the passageway 73, and the suction is delivered to the apertures 5 in the region of the electrosurgical device 3. In this way, suction is provided to whichever of the two devices (the cutting head 34 or the electrosurgical device 3) is being used at any particular time.

Figure 4A:
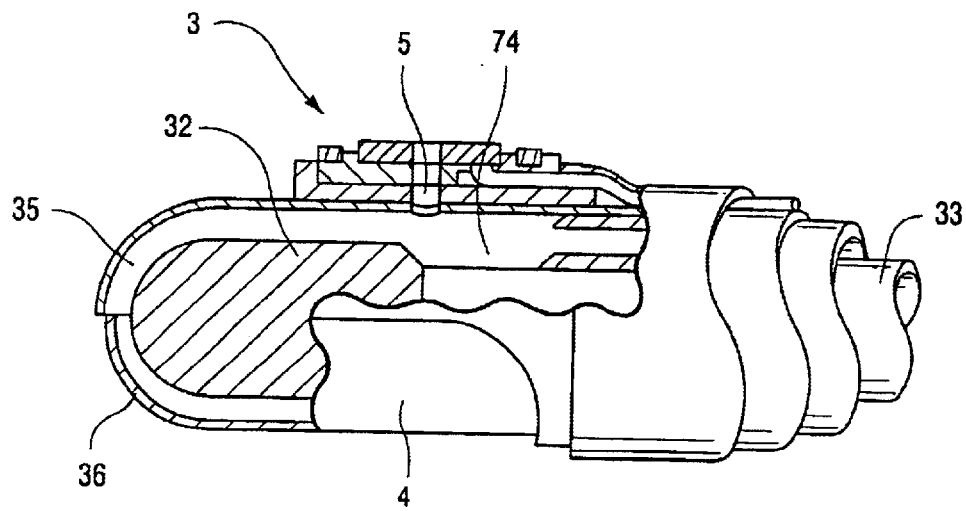
FIGS. 4a and 4b are side views, partly in section, of another alternative embodiment of a surgical instrument constructed in accordance with the invention.
Figure 4B:
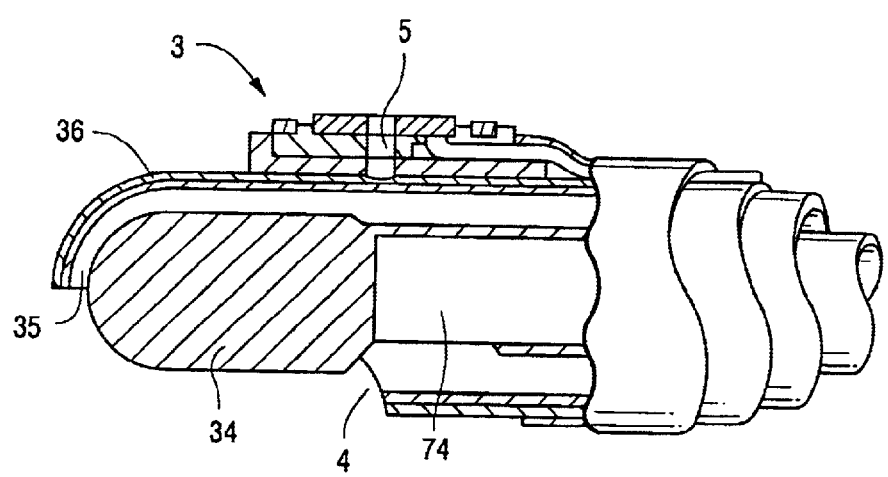

FIGS. 4a and 4b show a modified version of the surgical instrument, in which the stem 33 of the burr 32 is hollow and in communication with the suction pump 7. The stem 33 has an aperture 74 at its distal end to allow communication between the hollow interior of the stem and the cut-out 4. The instrument also has a curved baffle 36 at its distal end portion, the baffle being shaped to cover the inlet 35. The baffle 36 is rotatable between a first position, shown in FIG. 4a, and a second position, shown in FIG. 4b. In the first position, the baffle blocks the inlet 35, so that suction from the pump 7 is supplied through apertures 5 to the region of the electrosurgical device 3. In the second position, the baffle 36 is clear of the inlet 35, allowing suction to be supplied through the hollow interior of the stem 33 to the region of the abrasive cutting head 34 of the burr 32. As before, suction is provided to whichever of the two devices (the cutting head 34 or the electrosurgical device 3) is being used at any particular time.

What is claimed is:

1. A surgical instrument comprising an elongate hollow probe having an apertured region at its distal end portion, an elongate drive shaft disposed within the probe and mounted for rotation about its longitudinal axis within the probe, a cutting tool located at the distal end of the drive shaft and positioned adjacent to the apertured region, an electrosurgical device located at the distal end of the probe, a motor for rotating the drive shaft, and suction means for providing a source of suction at the apertured region for evacuating tissue debris removed by either the cutting tool or the electrosurgical device, wherein the apertured region is constituted by first and second apertures for evacuating the tissue debris, the cutting tool being positioned to enable tissue to be cut by cutting means provided on the cutting tool, the cutting means being engageable with tissue through the first aperture, and the second aperture being positioned in the region of the electrosurgical device.

2. A surgical instrument as claimed in claim 1, wherein the electrosurgical device is a bipolar electrosurgical device including at least one active electrode, at least one return electrode and an insulator for spacing and insulating the or each return electrode with respect to the or each active electrode.

3. A surgical instrument as claimed in claim 1, wherein the second aperture is positioned adjacent to the electrosurgical device.

4. A surgical instrument as claimed in claim 1, further comprising means for selectively blocking communication between the first aperture and the suction means to allow the suction means to operate principally through the second aperture.

5. A surgical instrument as claimed in claim 4, wherein the blocking means is provided by the cutting tool being configured in such a manner that a portion thereof effectively blocks the first aperture when the cutting tool is in a predetermined rotational position.

6. A surgical instrument as claimed in claim 5, wherein an outer surface of the hollow cutting tool constitutes the means for effectively blocking the first aperture when the cutting tool is in said predetermined position.

7. A surgical instrument as claimed in claim 5, further comprising means for selectively positioning the cutting tool automatically in said predetermined position.

8. A surgical instrument as claimed in claim 4, wherein the blocking means comprises a baffle operable to block effectively the first aperture.

9. A surgical instrument as claimed in claim 8, wherein the baffle is located on the exterior of the probe.

10. A surgical instrument as claimed in claim 8, where the baffle is located on the interior of the probe.

11. A surgical instrument as claimed in claim 8, wherein the baffle is movable between a first position, in which it effectively blocks the first aperture, and a second position in which it is clear of the first aperture.

12. A surgical instrument as claimed in claim 11, wherein the baffle is rotatable about the longitudinal axis of the probe between the first and second positions.

13. A surgical instrument as claimed in claim 8, wherein the baffle is manually movable between its first and second positions.

14. A surgical instrument as claimed in claim 8, wherein a motor is provided to move the baffle between its first and second positions.

15. A surgical instrument as claimed in claim 4, wherein the cutting tool is provided with an abrasive outer surface, the distal end portion of the probe being spaced from the abrasive outer surface to define an inlet through which tissue debris can pass.

16. A surgical instrument as claimed in claim 15, wherein the cutting tool is selectively movable longitudinally of the probe in order to provide the means for blocking communication between the first aperture and the suction means.

17. A surgical instrument as claimed in claim 1, wherein the drive shaft is hollow, the cutting tool is hollow and contiguous therewith, and the distal end portion of the cutting tool is formed with a cut-out through which tissue debris can be evacuated when the cut-out is in alignment with the first aperture.

18. A surgical instrument as claimed in claim 1, wherein there is a single active electrode, and a single return electrode, and the active electrode, the insulator and the return electrode are formed with contiguous apertures in alignment with the second aperture.

19. A surgical instrument as claimed in claim 1, wherein the drive shaft is solid and of a diameter less than that of the hollow probe so as to define a channel between the drive shaft and the hollow probe, tissue debris being removable via the channel.

* * * * *